United States Patent [19]
Arawa et al.

[11] 3,950,237
[45] Apr. 13, 1976

[54] COULOMETRIC TITRATING DEVICES

[75] Inventors: Kiyoshi Arawa; Seiji Ishikawa, both of Kitakyushi, Japan

[73] Assignee: Mitsubishi Kasei Kogyo Kabushiki Kaisha, Tokyo, Japan

[22] Filed: Mar. 31, 1975

[21] Appl. No.: 563,476

Related U.S. Application Data

[63] Continuation-in-part of Ser. No. 424,280, Dec. 13, 1973, abandoned.

[30] Foreign Application Priority Data

Dec. 14, 1972 Japan.............................. 47-125488

[52] U.S. Cl. .............................. 204/195 T; 324/29
[51] Int. Cl.² .................................... G01N 27/42
[58] Field of Search ............ 204/195 T, 1 T; 324/29

[56]  References Cited
UNITED STATES PATENTS

| | | | |
|---|---|---|---|
| 2,928,774 | 3/1960 | Leisey ................. | 204/1 T |
| 2,928,775 | 3/1960 | Leisey ................. | 204/1 T |
| 2,928,782 | 3/1960 | Leisey ................. | 204/195 T |
| 3,305,468 | 2/1967 | Liesch .................. | 204/195 T |
| 3,427,238 | 2/1969 | Myers et al. .......... | 204/195 T |
| 3,441,490 | 4/1969 | Johansson ............ | 204/195 T |
| 3,647,668 | 3/1972 | Lindblad et al. ...... | 204/195 T |

FOREIGN PATENTS OR APPLICATIONS

| 1,229,890 | 4/1971 | United Kingdom ............ 204/195 T |
|---|---|---|

OTHER PUBLICATIONS

Microcoulometric Titrating System, MCTS Data Sheet AI–II, p. 10, Dohrmann Inst. Co., Dec. 24, 1969.

*Primary Examiner*—G. L. Kaplan
*Attorney, Agent, or Firm*—Oblon, Fisher, Spivak, McClelland & Maier

[57]  ABSTRACT

An electric quantity titrating device is disclosed of the type comprising electrolytic electrodes immersed in a solution to be analyzed for passing electrolytic current, detecting electrodes immersed in the solution, detecting apparatus connected across the detecting electrodes for producing a voltage signal which is used to continuously supply the electrolytic current to the electrolytic electrodes and integrating apparatus for integrating the electrolytic current for measuring the electric quantity required for the analysis until an end point is reached. A current controlling apparatus is provided in this system which includes a device for detecting the deviation of the voltage signal from a preset value at the end point, an amplifier for amplifying the deviation signal, and a current converter for converting the amplifed current into output current which is applied to the electrolytic electrodes. The integrating apparatus includes a device for converting the output from the current converter into a pulse train, and a counter for counting the pulse train.

14 Claims, 11 Drawing Figures

COULOMETRIC TITRATING DEVICES

CROSS REFERENCE TO RELATED APPLICATION

This application is a continuation-in-part application of Ser. No. 424,280 filed Dec. 13, 1973 entitled COULOMETRIC TITRATING DEVICES, now abandoned.

BACKGROUND OF THE INVENTION

This invention relates to a titrating device wherein electrolytic current is supplied continuously and controlled to titrate the quantity of electricity so as to automatically perform qualitative analysis of the moisture or electrolizable substances contained in a sample.

According to a prior art coulometric titrating device an electrolytic current of a definite value is on-off controlled and the interval of current conduction is integrated for measuring the electric quantity required for the electrolysis until an end point is reached. However, such prior art device has the following disadvantages.

a. It is necessary to pass current of a constant value from the beginning to the end of the measurement. Thus, it is necessary to interrupt large electrolytic current near the end point so that it is impossible to perform accurate analysis by finely adjusting the current. Consequently, the accuracy of the measurement is limited. Especially, the accuracy of the analysis of small quantities is low.

b. As it is necessary to maintain the accuracy of the analysis in a prescribed range it is not permitted to increase the electrolytic current beyond a certain value with the result that analysis of large quantities requires long times.

c. Since the integration of the electric quantity is performed by a time integration of a constant current, it is usually necessary to maintain the current at a constant value and the range of measurement is limited to a narrow one in view of the accuracy and time of analysis.

d. Since a constant current is used, when the resistivity of the solution is increased beyond a certain value, the electrolytic current of a set value will not flow thus disenabling the measurement. For this reason, there is a lower limit for the electric conductivity of the solution to be analyzed.

e. When the blank caused by such factors as a sample, a reagent or an electrolytic reaction cell increases, the end point becomes unstable, thus causing measuring errors, and in an extreme case it is impossible to measure.

SUMMARY OF THE INVENTION

Accordingly, it is an object of this invention to provide an improved electric current titrating device capable of eliminating various disadvantages of the prior art device described above and which can reduce the analysis time, improve the accuracy of analysis, can analyze at high accuracy an extremely small quantity as well as solutions having low electroconductivity.

According to this invention there is provided a coulometric titrating device of the type wherein a solution of a substance to be analyzed is electrolyzed by passing electrolytic current across electrolytic electrodes immersed in the solution and the electrolytic current is integrated to measure the electric quantity required for the electrolysis until an end point is reached, characterized in that there are provided detecting electrodes immersed in the solution, detecting means connected across the detecting electrodes for producing a voltage signal, a current controller for converting the voltage signal into electric current proportional to the deviation of the voltage signal from the value thereof at the end point, means for continuously supplying the electric current to the electrolytic electrodes to act as the electrolytic current, and means for integrating the electrolytic current.

DESCRIPTION OF THE PREFERRED EMBODIMENTS

Figure 1:
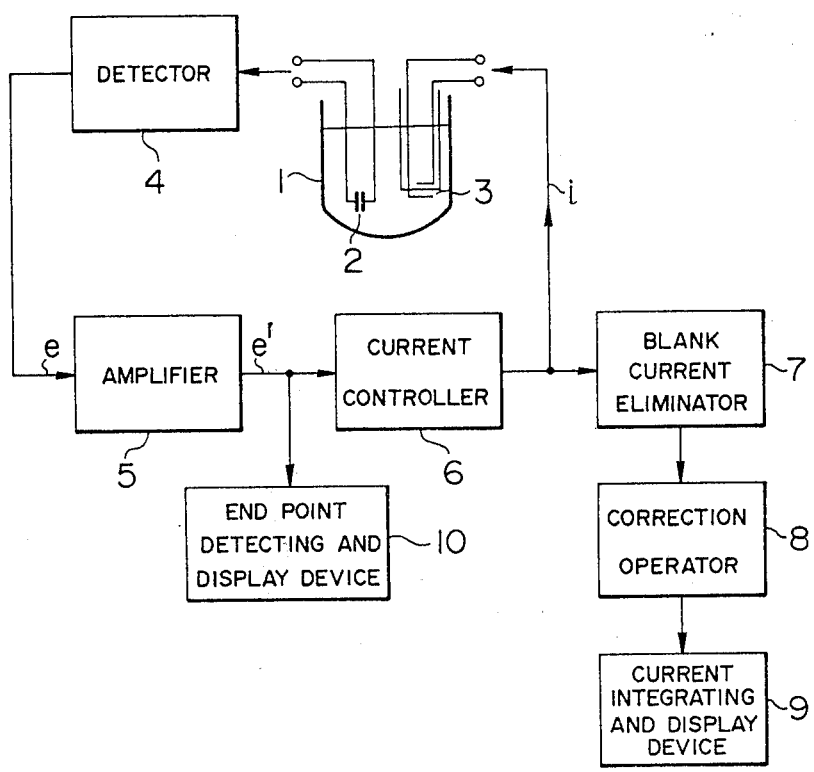
FIG. 1 is a block diagram showing one embodiment of this invention.

A preferred embodiment of the coulometric titrating device shown in FIG. 1 comprises an electrolytic reaction cell 1 containing detecting electrodes 2 and electrolytic electrodes 3 which are immersed in a solution of a substance to be analyzed. An electric signal produced by detecting electrodes 2 is applied to an amplifier 5 through a detector 4 and the amplifed current is applied to a current controller 6 which converts the amplified signal into a current output proportional to the deviation of the amplified signal from an end value and the output is applied to the electrolytic electrode 3 as an electrolytic current i.

If desired, the electrolytic current i may be passed through a blank current eliminator 7 and the output from the eliminator 7 is applied to a correction operator 8 to perform a conversion of the unit from the electric current value to the analyzed value in milligram, for example, and the correction of the amount in PPM, for example, of the sampled quantity of the sample for representing the ratio thereof with respect to the sample. The output from the correction operator 8 is applied to a current integrating and display device 9 to directly display the analyzed value corresponding to the electric quantity. After being converted into a proportional voltage signal by the blank current eliminator 7 the electrolytic current is converted into a signal from which blank current has been eliminated. This signal is then converted by the correction operator 8 into a signal corresponding to the electrochemical equivalent according to the Law of Faraday. Then the output signal from the correction operator 8 is applied to the current integrating and display device 9 to be converted into a pulse train of the number proportional to the value of the output signal. The pulse train is then counted by a counter, the count thereof corresponding to the value of total integration of the electrolytic current. The detection of the end point is performed by applying a portion of the output of the amplifier 5 to the end point detecting and display device 10 which displays the detected end point when the level of the detected voltage exceeds a predetermined level.

Figure 2:
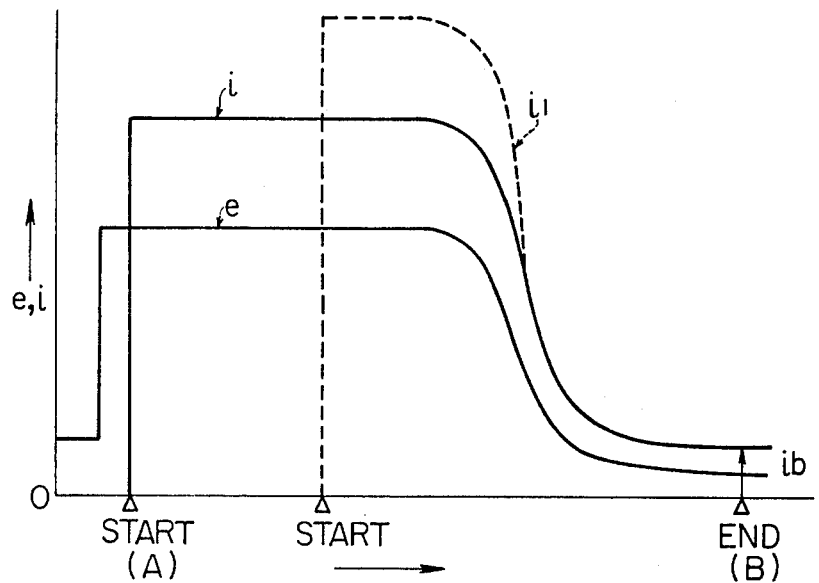
FIG. 2 is a graph showing the relationship between the detected voltage and the electrolytic current.

FIG. 2 show one example of the relationship between the electrolytic current $i$ utilized for the analysis and the voltage output $e$ from detector 4.

When the titration is started at a starting point A, electrolytic current $i$ flows which is proportional to the deviation of the detector output $e$ from the value thereof at the end point. As the titration proceeds both detector output $e$ and electrolytic current $i$ decrease. Near the end point the electrolytic current $i$ converges toward a definite value in accordance with the detector output voltage $e$ and at the end point the electrolytic current $i$ becomes equal to a constant blank current $ib$. Consequently, the end point can be determined by detecting the definite electrolytic current or the end point level of the detector output voltage $e$.

The electric quantity is determined by continuously integrating current itself irrespective of the magnitude and duration thereof. Conversion of the unit of the electric quantity into that of the analyzed value and the correction of the sampled quantity of the sample is performed by the correction operator 8 in terms of current value prior to performing current integration. The setting of the proportionality is done by the suitable selection of the gain of amplifier 5 or current controller 6, and the value of the electrolytic current is determined in accordance with the detector output voltage $e$ at the ratio of the proportionality gain.

Where a large proportionality gain is selected the electrolytic current assumes a large value shown by $i_1$ thereby reducing the time of analysis proportionally.

The detail of various components of the coulometric titrating device of the invention will now be described.

The purpose of detector 4 is to detect the voltage between detecting electrodes 2 and to convert it into a D.C. voltage signal isolated from electrodes 2.

Figure 3:
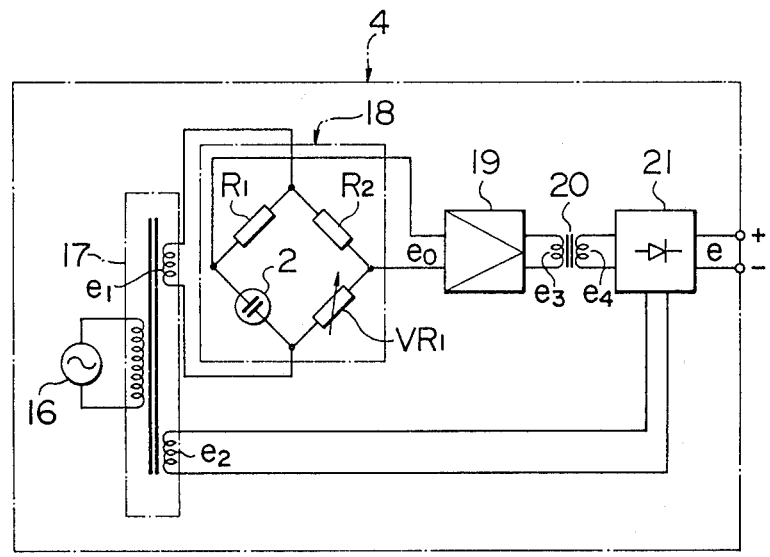
FIG. 3 shows a connection diagram of one example of a detecter utilized in this invention.

FIG. 3 shows one example of the detector which comprises an AC bridge utilizing the electrodes 2 as its one arm and energized by AC voltage $e_1$ supplied from an AC source 16 through a transformer 17. The unbalanced voltage output $e_0$ from the AC bridge 18 is converted into an output $e_4$ which is isolated from the electrodes by means of an insulating transformer 20. This output $e_4$ is rectified by a synchronous rectifier 21 under control of the output voltage $e_2$ of transformer 17 to provide a DC output $e$. In this manner, the variation in the impedance across electrodes 2 is converted into DC output voltage isolated from the electrodes 2. One arm $VR_1$ is adjusted such that the bridge reaches a balanced condition just at the end point to reduce the output voltage $e_0$ to zero.

The disclosed detector has the following advantages.

1. Since AC voltage is impressed across the detecting electrodes the output voltage will not be affected by the noises caused by the DC potential difference of the solution due to the electrolytic current so that the output voltage is quite independent of the variation in the electrolytic current, and the stirring of the solution. For this reason, the detected output voltage is extremely stable whereby it is possible not only to provide an accurate control of the electrolytic current but also improve the accuracy of analysis and reproduceability.

2. Since alternating output voltage is detected, isolation of the circuit including the detecting electrodes from the electrolytic electrodes can be readily provided by using an insulation transformer.

3. Since a bridge circuit is used, it is possible to make perfectly zero the bridge output at the end point, thus improving the sensitivity and accuracy of the detection at the end point.

Furthermore, by balancing the bridge at the end point, any variation in the source voltage does not affect the result of measurement at the end point. Accordingly, it is not necessary to use a source of constant current or constant voltage.

It should be understood that the detecting system is not limited to those described above and that the following systems can also be used. More particularly, among these systems are included a DC constant current differential voltage system wherein constant direct current is passed across the detecting electrodes 2 and the voltage drop thereacross is used as the detected output voltage, a DC bridge detecting system wherein the detecting electrodes are included in one arm of a DC bridge circuit, the variation in the voltage across the detecting electrodes is taken out as the unbalanced voltage of the bridge circuit which is used as the detected output voltage, an AC constant current differential voltage detecting system wherein constant alternating current is passed across the detecting electrodes and the voltage across the detecting electrodes is used as the detected output voltage, and an AC constant voltage differential current detecting system wherein constant AC voltage is impressed across the detecting electrodes, the current flowing thereacross is derived out in terms of the voltage drop across a series resistor and the voltage drop is utilized as the detected output voltage.

Figure 9:
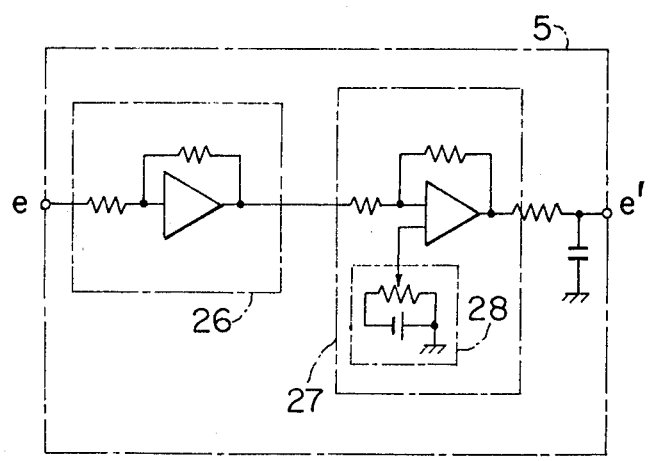
FIG. 9 is a connection diagram showing the details of amplifier 5 shown in FIG. 1.

The details of one example of the amplifier 5 are shown in FIG. 9 in which the detected signal $e$ from detector 4 is amplified by an amplifier 26 and the amplified voltage is compared with a voltage set by an end voltage setter 28 by the operation of an end voltage subtractor 27. The difference thus obtained provides the output of amplifier 5. In this manner, the output of amplifier 5 is a DC voltage $e'$ corresponding to the deviation of the detected signal voltage $e$ from a pre-set end value.

In the titration device of this invention the electrolytic current may be controlled to be always proportional to the output voltage but it is important to precisely control the electrolytic current near and at the end point. For this reason, the control until a point near the end point may be coarse or the control until that point may be omitted provided that a suitable value of the electrolytic current is suitably selected.

Figure 4:
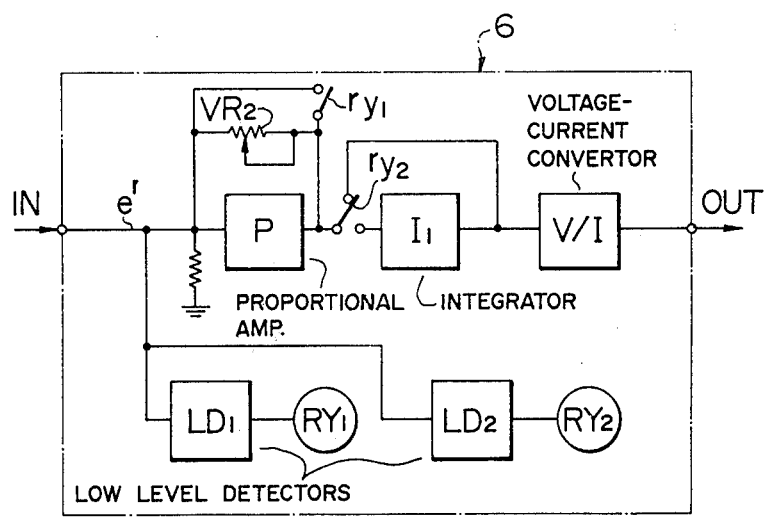
FIG. 4 shows a connection diagram of one example of a current controller utilized in this invention.

The following is a typical example of the current controller utilized in this invention. In FIG. 4, a voltage $e'$ which is the output of amplifier 5 (FIG. 4) that is the difference between the detected signal voltage 3 and the pre-set end value is applied to an input terminal IN of the current controller 6 and is then applied to low imput level detectors $LD_1$ and $LD_2$, respective outputs thereof being utilized to drive a proportionality gain switching relay $RY_1$ and an integration initiating relay $RY_2$. With this arrangement until a point near the end point is reached the input voltage is high so that both relays $RY_1$ and $RY_2$ are maintained off.

Until the point near the end point is reached contact $ry_2$ of relay $RY_2$ is held in the position shown so that the voltage $e'$ is applied to a voltage-current converter V/I through a proportional amplifier P whose gain is determined by a proportionality gain setting variable resistor $VR_2$, and around an integrator $I_1$, thus producing a current output $i$ on output terminal OUT. This current output $i$ which is proportional to the proportionality gain set by variable resistor $VR_2$ is applied across the electrolytic electrodes.

Near the end point, as the input voltage decreases to a preset level, the low input level relay $LD_1$ operates to energize relay $RY_1$ thus closing its contact $ry_1$ for switching to the most suitable low proportionality gain. As a result, near and at the end point it is possible to always assure adequate control irrespective of the setting of the variable resistor $VR_2$. At a point closer to the end point, the low input level detector $LD_2$ operates to energize relay $RY_2$, thus switching its contact $ry_2$. Then, the output from proportional amplifier P flows through integrator I so as to eliminate the offset input voltage for the blank current by the integrating action of the integrator.

For the reason described above, the amplified output voltage is always zero at the endpoint thus enabling accurate detection of the end point with a high reproduceability.

The noise which may enter into the signal can be eliminated by adding a CR filter. In such a case, however, it is advantageous to add a differentiating circuit to compensate for a delay of the signal caused by the CR filter.

Figure 5:
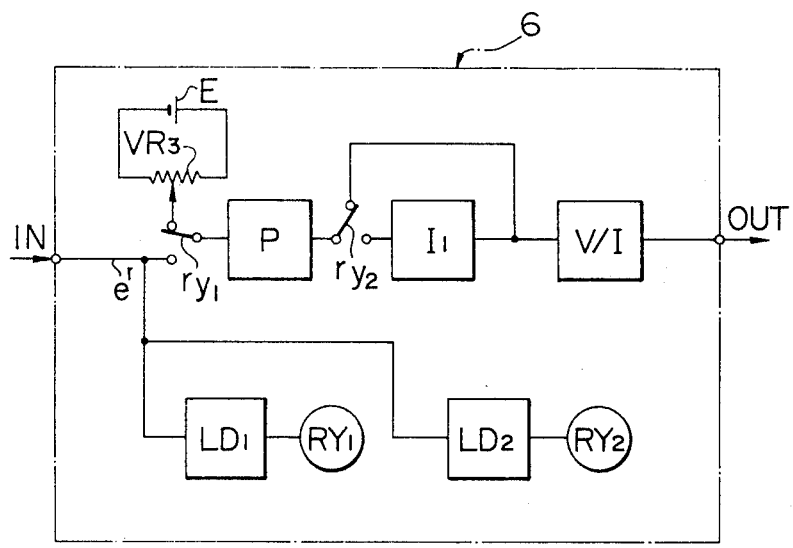
FIG. 5 shows a connection diagram of another example of the current controller.

Still another type of current controller can also be used. More particularly, as shown in FIG. 5, the output voltage $e'$ of amplifier 5 (see FIG. 1) is applied to the low input level detectors $LD_1$ and $LD_2$ through input terminal IN of current controller 6 for energizing control input switching relay $RY_1$ and integration initiation relay $RY_2$. The circuit shown in FIG. 5 is different from that shown in FIG. 4 in that the variable resistor $VR_3$ is energized from an independent source E instead of input voltage $e'$ whereby the electrolytic current is controlled at a constant value determined by the setting of the variable resistor until a point near the end point is reached, whereas thereafter the electrolytic current is controlled in proportion to the detected output voltage $e'$.

With the connection shown in FIG. 5, since the input voltage is high until a point near the end point is reached both relays $RY_1$ and $RY_2$ are held off. Accordingly, until that point is reached, the output provided by the variable resistor $VR_3$ for adjusting the electrolytic current is applied to the voltage-current converter V/I through proportional amplifier P and around integrator $I_1$ thus producing a current output $i$ at the output terminal OUT. This output current is proportional to the setting of varibale resistor $VR_3$ and is applied across the electrolytic electrode.

Near the end point, as the input voltage $e'$ decreases to a predetermined low level, the low input level detector $LD_1$ operates to energize relay $RY_1$ whereby its contact $ry_1$ is switched to apply input voltage $e_1$ to the proportional amplifier P. Thereafter, the electrolytic current is controlled in proportion to the input voltage $e'$.

At a point more closer to the end point the input voltage $e'$ decreases further and another low input level detector $LD_2$ operates to energize relay $RY_2$ thus switching its contact $ry_2$ to the side of integrator $I_1$. Accordingly, the output of the proportional amplifier P is integrated by integrator $I_1$ thereby eliminating the offset input voltage for the blank current. For this reason, the amplified output voltage becomes zero at the end point thus enabling accurate detection of the end point at a high reproduceability. In an electrolytic reaction cell for titrating an electric quantity, the blank current caused by the ionization reaction of such external substance as gas is generally different from the electrolytic current of the substance to be analysed, there is a fear that such external substance adversely effects the result of titration. Accordingly, it is advantageous to incorporate blank current eliminator 7 (FIG. 1) so as to subtract the blank current thereby integrating only the electrolytic current for the substance to be analyzed.

Figure 6:
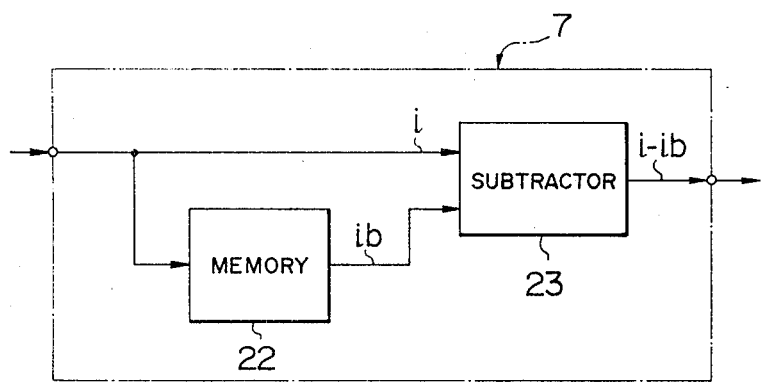
FIG. 6 shows a connection diagram of a blank eliminator utilized in this invention.
Figure 11:
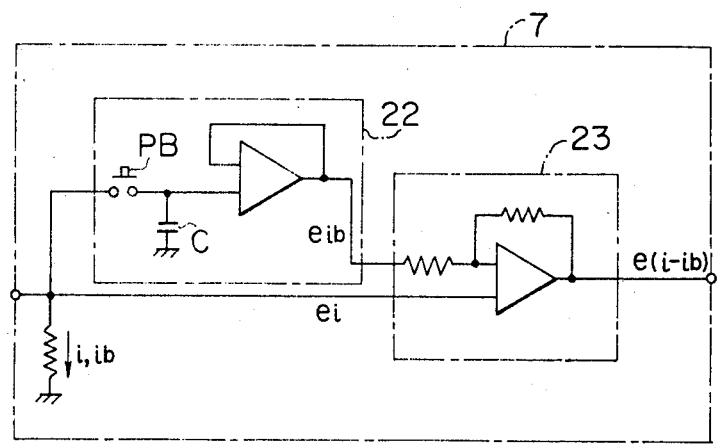
FIG. 11 is a connection diagram showing the details of blank current eliminator 7 shown in FIG. 1.

One example of the blank eliminator 7 is shown in FIGS. 6 and 11 and comprises a blank current memory device 22 and a subtractor 23. A voltage eib corresponding to the blank current ib at the end of the previous analysis is stored in a memory capacitor C by depressing a push button $P_B$. At the time of the next analysis, by the operation of the subtractor 23 shown as a differential operational amplifier, voltage eib corresponding to the blank current ib is subtracted from the voltage ei corresponding to the electrolytic current $i$. As a result a voltage $e$ $(i - ib)$ corresponding to the difference $(i - ib)$ is applied to the integrating device 9, thus eliminating the blank current.

Figure 10:
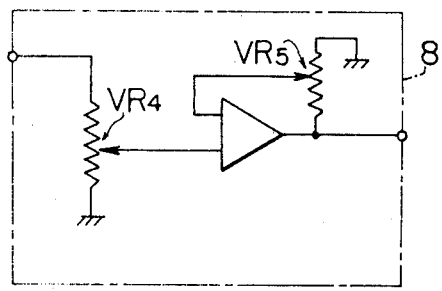
FIG. 10 is a connection diagram showing the details of the correction operator 8 utilized in this invention.

The details of one example of the correction operator 8 are shown in FIG. 10. The voltage $e$ $(i - ib)$ corresponding to the electrolytic current i from which the blank current has been subtracted by the action of the blank current eleminator 7 is applied to one terminal of a potentiometer resistor $VR_4$ which is used to set the unit conversion coefficient for an electric quantity and the analyzed value. A potentiometer resistor $VR_5$ for adjusting the amount of negative feedback is provided for setting the correction coefficient for an amount of the specimen sampled. As a consequence, the unit of the signal from the blank current elimination 7 is converted by the operation of potentiometer $VR_4$ and is subjected to the correction operation of the amplifier.

The electrolytic current is applied to a correction operator shown in FIG. 10 as a voltage signal and converted into a signal whose value has been converted into an electro-chemical equivalent according to the Law of Faraday. The circuit constant (which is determined by variable resistors $VR_4$ and $VR_5$) of the correction operator is set to perform such conversion operation.

Figure 7:
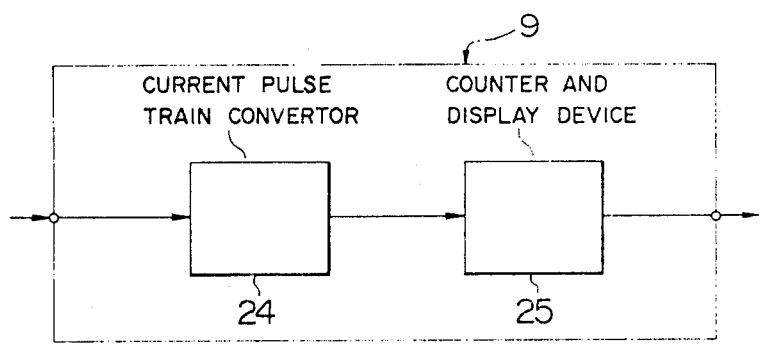
FIG. 7 shows a connection diagram of one example of a current integrating and display device.

One example of the current integrating and display device 9 that can be used in this invention is illustrated in FIG. 7 and comprises a current-pulse train convertor 24 and a counter and display device 25. The current-pulse train converter 24 functions to convert a current input into a continuous pulse train of the number proportional to the value of the input current and the number of the pulses is counted and displayed by the counter and display device 25.

The current-pulse train converter 24 may be a V/F converter such as model 4701 sold by Teledyne Philbrick Co., U.S.A. or model 801A sold by Dynamic Measurement Corp., U.S.A.

Figure 8:
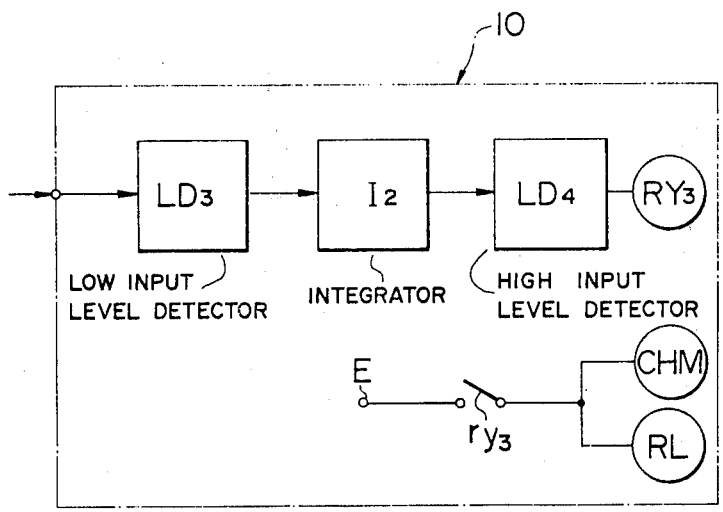
FIG. 8 shows a connection diagram of one example of an end point detecting display device utilized in this invention.

FIG. 8 illustrates one example of the end point detecting and display device 10 utilized in this invention. This device comprises a low input level detector $LD_3$ connected to receive the amplified output voltage for detecting the low voltage level at or near the end point or a balancing point. Thus, as the input voltage decreases to a predetermined low level close to zero at a point near the end point the detector $LD_3$ produces an output to cause integrator $I_2$ to commence an integral operation.

After a predetermined interval when the output of the integrator $I_2$ reaches a predetermined level, a high input level detector $LD_4$ operates to energize relay $RY_3$ which closes its contact $ry_3$ to operate an alarm CHM and a lamp RL, thus informing that the end point is reached.

To detect the balanced point at the end point the detected voltage is passed through a differentiating circuit, not shown, the detect the level at which the output thereof becomes zero.

When compared with a conventional coulometric titrating device wherein the electrolytic current is on-off controlled to integrate the current conduction time, this invention has the following advantages.

I. Near the end point, the detected voltage becomes extremely small and the electrolytic current is finely controlled in proportion to the detected voltage so that the accuracy of measurement is greatly improved over that of the prior art.

II. As it is possible to freely select any value of the electrolytic current by the suitable setting of the proportionality gain it is possible to greatly reduce the time required for analyzing a large quantity of substance by increasing the electrolytic current.

III. Similarly, a small quantity can be analyzed with small current with high accuracy.

IV. As it is not always necessary to use constant current for the electrolysis, even when the resistivity of the solution increases, it is possible to continue analysis with the reduced current. Accordingly, it is possible to efficiently analyze solutions having low electroconductivity and hence difficult to pass electrolytic current of sufficient intensity.

V. In a case where the blank current is large and the blank is not stable, it is possible to readily determine at high accuracy the end point by detecting the level of the detected output voltage or the balancing point of the electrolytic current.

What is claimed as new and desired to be secured by Letters Patent in the United States is:

1. In an electric quantity titrating device of the type comprising electrolytic electrodes immersed in a solution of a substance to be analyzed for passing electrolytic current through said solution, detecting electrodes immersed in said solution, detecting means connected across said detecting electrodes for producing a voltage signal which is used to continuously supply said electrolytic current to said electrolytic electrodes and means for integrating said electrolytic current for measuring the electric quantity required for the analysis until an end point is reached, the improvement which comprises:

means for controlling electric current including means for detecting the deviation of said voltage signal from a preset value thereof at the end point, an amplifier for amplifying the deviation signal, a current converter for converting the amplified signal into output current, and means for supplying said output current to said electrolytic electrodes, and wherein said integrating means includes means for converting the output from said current converter into a pulse train, and means for counting said pulse train.

2. The coulometric titrating device according to claim 1 which further comprises a blank current eliminater connected between the output of said current controlling means and said integrating means.

3. The coulometric titrating device according to claim 2 which further comprises a correction operator connected between said blank current eliminater and said integrating means for converting the unit of the electric quantity into that of the analyzed value and for correcting the sample quantity.

4. The current quantity titrating apparatus according to claim 2 wherein said blank eliminator comprises a memory device for storing the blank current at the end of a previous analysis and a subtractor for subtracting said blank current from the electrolytic current during subsequent analysis.

5. The coulometric titrating device according to claim 1 which further comprises an end point detecting means connected to receive said voltage signal.

6. The coulometric titrating device according to claim 5 wherein said end point detecting means comprises an integrator, means for initiating the operation of said integrator when said voltage signal reaches a predetermined low level, and means responsive to the output of said integrator for operating an alarm or display device when the output from said integrator reaches a predetermined high level.

7. The coulometric titrating device according to claim 1 wherein said detecting means comprises means for passing constant alternating current across said detecting electrodes and means for detecting the voltage drop across said detecting electrodes to produce said voltage signal.

8. The coulometric titrating device according to claim 1 which further comprises a correction operator connected between the output of said current controlling means and said integrating means for converting the unit of the electric quantity into that of the analyzed value and for correcting the sampled quantity of the sample.

9. The electric quantity titrating device according to claim 1 wherein said detecting means comprises an AC bridge circuit including said detecting electrodes as one arm thereof, an amplifier connected across the output terminals of said bridge circuit, and an insulating transformer connected to the output of said amplifier to electrically isolate the secondary voltage of the insulating transformer from said detecting electrodes.

10. The coulometric titrating device according to claim 1 wherein said detecting means comprises means for passing constant direct current across said detecting electrodes, and means for detecting the voltage drop across said detecting electrodes for producing said voltage signal.

11. The coulometric titrating device according to claim 1 wherein said detecting means comprises a DC bridge circuit including said detecting electrodes as one arm thereof and means for deriving out the unbalanced output of said DC bridge circuit as said voltage signal.

12. The coulometric titrating device according to claim 1 wherein said detecting means comprises means for applying constant alternating voltage across said detecting electrodes and means for detecting the current flowing across said detecting electrodes to produce said voltage signal.

13. The coulometric titrating device according to claim 1 wherein said current controller comprises a proportional amplifier, an integrator, a voltage-current converter connected to the output of said integrator, means for determining the proportionality gain of said proportional amplifier, a low level detector responsive to said voltage signal, and means for supplying the output from said voltage-current converter to said electrolytic electrodes as the electrolytic current, whereby until a point near the end point is reached said voltage signal is applied to said voltage-current converter through said proportional amplifier and around said integrator whereas near said end point said voltage signal is applied to said voltage-current converter through said proportional amplifier and said integrator.

14. The coulometric titrating apparatus according to claim 13 wherein said means for determining the proportionality gains of said amplifier and said low level detecter are arranged such that until a point near the end point is reached said electrolytic current is controlled at a constant rate determined by said proportionality gain determining means, whereas thereafter said electrolytic current is controlled in proportion to said voltage signal.

* * * * *

UNITED STATES PATENT AND TRADEMARK OFFICE
CERTIFICATE OF CORRECTION

PATENT NO. : 3,950,237
DATED : April 13, 1976
INVENTOR(S) : Arakawa, et al

It is certified that error appears in the above-identified patent and that said Letters Patent are hereby corrected as shown below:

Please change the last name of one of the inventors from "Arawa" to --Arakawa--.

Signed and Sealed this

Fourteenth Day of September 1976

[SEAL]

Attest:

RUTH C. MASON
*Attesting Officer*

C. MARSHALL DANN
*Commissioner of Patents and Trademarks*